United States Patent
Han et al.

(10) Patent No.: US 9,802,874 B2
(45) Date of Patent: *Oct. 31, 2017

(54) ETHYLENE TETRAMERIZATION CATALYST SYSTEMS AND METHOD FOR PREPARING 1-OCTENE USING THE SAME

(71) Applicants: SK INNOVATION CO., LTD., Seoul (KR); SK GLOBAL CHEMICAL CO., LTD., Seoul (KR)

(72) Inventors: Taek Kyu Han, Daejeon (KR); Myung Ahn Ok, Daejeon (KR); Sung Seok Chae, Daejeon (KR); Sang Ook Kang, Seoul (KR); Jae Ho Jung, Incheon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 688 days.

This patent is subject to a terminal disclaimer.

(21) Appl. No.: 14/086,530

(22) Filed: Nov. 21, 2013

(65) Prior Publication Data

US 2014/0081064 A1     Mar. 20, 2014

Related U.S. Application Data

(62) Division of application No. 12/449,001, filed on Dec. 23, 2009, now Pat. No. 8,609,924.

(30) Foreign Application Priority Data

Jan. 18, 2007   (KR) .................. 10-2007-0005688

(51) Int. Cl.
*C08F 4/69* (2006.01)
*B01J 31/26* (2006.01)
*C07C 2/34* (2006.01)
*B01J 31/24* (2006.01)
*C07C 2/26* (2006.01)

(52) U.S. Cl.
CPC .............. *C07C 2/34* (2013.01); *B01J 31/24* (2013.01); *B01J 31/2404* (2013.01); *B01J 31/2409* (2013.01); *C07C 2/26* (2013.01); *B01J 2231/20* (2013.01); *B01J 2531/62* (2013.01); *C07C 2531/14* (2013.01); *C07C 2531/22* (2013.01); *C07C 2531/24* (2013.01)

(58) Field of Classification Search
None
See application file for complete search history.

(56) References Cited

U.S. PATENT DOCUMENTS 8,309,779 B2 * 11/2012 Han ................ B01J 31/24
585/502

FOREIGN PATENT DOCUMENTS

WO    WO 2009002770    *   2/2009  ............... C08F 4/69

* cited by examiner

*Primary Examiner* — Yun Qian
(74) *Attorney, Agent, or Firm* — Abelman, Frayne & Schwab

(57) ABSTRACT

Disclosed herein is a method of preparing 1-octene at high activity and high selectivity while stably maintaining reaction activity by tetramerizing ethylene using a chromium-based catalyst system comprising a transition metal or a transition metal precursor, a cocatalyst, and a P—C—C—P backbone structure ligand represented by $(R^1)(R^2)P$—$(R^5)CHCH(R^6)$—$P(R^3)(R^4)$.

11 Claims, 2 Drawing Sheets

ETHYLENE TETRAMERIZATION CATALYST SYSTEMS AND METHOD FOR PREPARING 1-OCTENE USING THE SAME

CROSS-REFERENCE TO RELATED APPLICATIONS

This application is a Divisional Application of Ser. No. 12/449,001, filed Dec. 23, 2009 which claims the priority of Korean Application No. 10-2007-0005688, filed Jan. 18, 2007, all of which are incorporated herein by reference.

TECHNICAL FIELD

The present invention relates to a catalyst system for tetramerizing ethylene and a method of preparing 1-octene by tetramerizing ethylene using the catalyst system.

BACKGROUND ART 1-octene, which is a monomer or comonomer for producing linear low-density polyethylene, is a commercially important raw material which is widely used in a polymerization process and is used as a specific drug.

Higher α-olefins, necessary for producing linear low-density polyethylene, are obtained through an ethylene oligomerization reaction. However, the ethylene oligomerization reaction is inefficient in that a large amount of butene, octene, derivatives of octene and specific higher oligomers are formed together with polyethylene.

In conventional ethylene oligomerization technologies, generally, various α-olefins are formed depending on the Schulz-Flory or Poisson product distribution, and thus the yield of desired products is limited. In relation to this, U.S. Pat. No. 6,184,428 discloses a nickel-based catalyst comprising 2-diphenyl phosphino benzoic acid as a chelate ligand, $NiCl_2 \cdot 6H_2O$ as a nickel precursor, and sodium tetraphenyl borate as a catalyst activator. It is also disclosed in this patent document that, in the oligomerization of ethylene using the nickel-based catalyst, the selectivity of 1-octene is 19%.

Further, German Patent No. 1,443,927 and U.S. Pat. No. 3,906,053 disclose Ziegler catalysts produced based on a trialkyl aluminum catalyst. It is also disclosed in these patent documents that 13~15 wt % of 1-octene, based on the total amount of an olefin mixture, can be produced using the Ziegler catalyst.

Recently, research on methods of producing 1-octene by selectively tetramerizing ethylene through transition metal catalysis has been conducted. Here, most commonly-known transition metal catalysts are chromium-based catalysts.

Recently, it was disclosed in WO 04/056479 that 1-octene is produced by tetramerizing ethylene using a chromium-based catalyst including a hetero atom ligand having phosphorus and nitrogen as heteroatoms. Here, examples of the heteroatom ligand, which is used for an ethylene tetramerization catalyst, may include $(phenyl)_2PN(isopropyl)P(phenyl)_2$ and the like.

It is also disclosed in the above conventional technology that 1-octene can be produced at a selectivity of more than 70 wt % by tetramerizing ethylene using a chromium-based catalyst including a heteroatom ligand having phosphorus and nitrogen as heteroatoms without substituents that are polar to hydrocarbyl groups or heterohydrocarbyl groups, which are bonded with phosphorus.

However, conventional technologies are problematic in that, in relation to the structure of ligands including heteroatoms, specifically, they cannot clearly demonstrate the highly selective production of 1-octene by tetramerizing ethylene when catalysts include what kind of ligand, in that they can present only a PNP backbone structure ligand, for example, $(R^1)(R^2)P$—$(R^5)N$—$P(R^3)(R^4)$, as a ligand having a 1-octene selectivity of about 70 wt %, and in that the structure of the substituents of the ligands including heteroatoms is also limitedly disclosed. Further, the conventional PNP backbone structure ligand having heteroatoms is also problematic in that, in the preparation of 1-octene, reaction activity cannot be maintained constant, and the reaction rate is also rapidly decreased with the reaction of time.

DISCLOSURE

Technical Problem

The present inventors overcame the above problems by finding that a chromium-based catalyst system having a P—C—C—P backbone structure ligand containing no nitrogen can be used to form 1-octene by tetramerizing ethylene at a selectivity of more than 70 wt %, and that the activity of the chromium-based catalyst system is maintained stable, and thus the decrease in reaction rate with reaction time can be prevented. Based on the finding, the present invention was completed.

Accordingly, the present invention has been made keeping in mind the above problems occurring in the prior art, and an object of the present invention is to provide a method of preparing 1-octene at high activity and high selectivity while stably maintaining reaction activity by tetramerizing ethylene using a chromium-based catalyst system comprising a transition metal or a transition metal precursor, a cocatalyst, and a P—C—C—P backbone structure ligand represented by the following Formula 1:

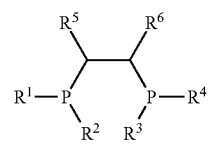

[Formula 1]

Technical Solution

In order to accomplish the above object, the present invention provides a catalyst system for tetramerizing ethylene, comprising a transition metal or a transition metal precursor, a cocatalyst, and a P—C—C—P backbone structure ligand represented by Formula 1 below:

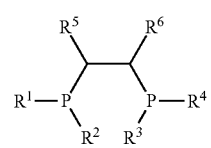

[Formula 1]

wherein $R^1$, $R^2$, $R^3$ and $R^4$ are each independently a hydrocarbyl group, a substituted hydrocarbyl group, a heterohydrocarbyl group and a substituted heterohydrocarbyl group, each of the $R^1$, $R^2$, $R^3$ and $R^4$ has no substituent on an atom adjacent to the atom bonded with P, and $R^5$ and $R^6$ are not hydrogen but each independently a hydrocarbyl group and substituted hydrocarbyl group.

Advantageous Effects

When ethylene is tetramerized using the chromium-based catalyst system including a P—C—C—P backbone structure ligand according to the present invention, it is advantageous in that highly pure 1-octene can be prepared because the chromium-based catalyst system has high catalytic activity and high 1-octene selectivity, and in that the activity of the chromium-based catalyst system is maintained stable, and thus the decrease in reaction rate with reaction time can be prevented.

BEST MODE

Figure 1:
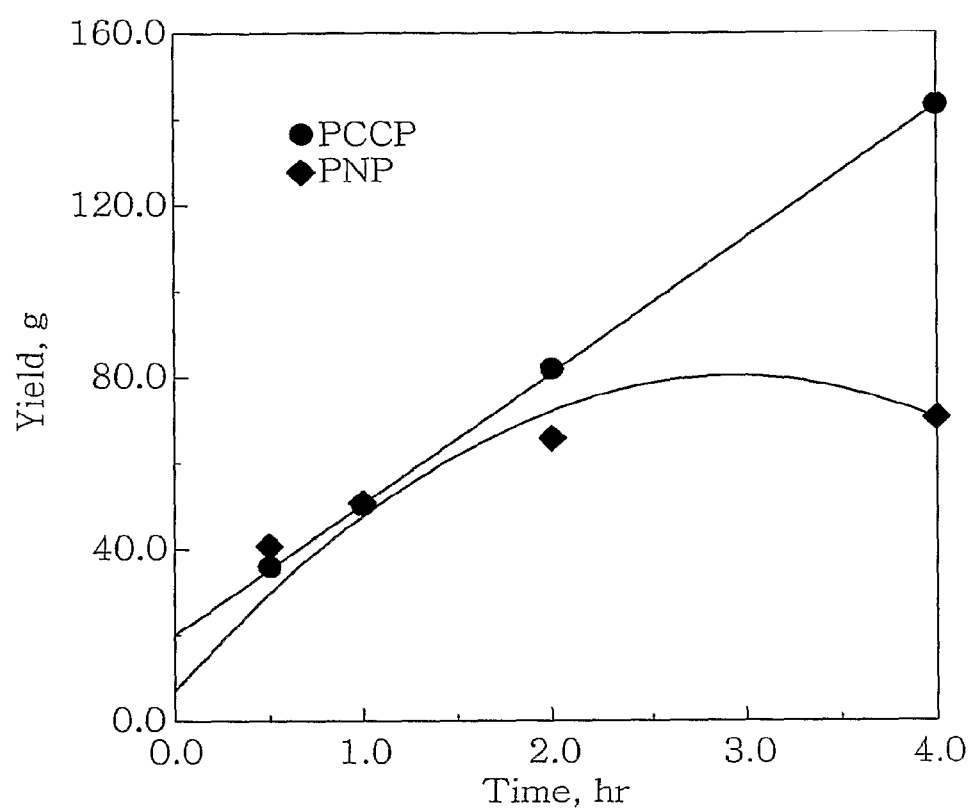
FIG. 1 is a graph showing the change in catalytic activity in the ethylene tetramerization reaction using a catalyst system according to the present invention.

Hereinafter, the present invention will be described in detail.

The present invention provides a catalyst system for tetramerizing ethylene, comprising a transition metal or a transition metal precursor, a cocatalyst, and a P—C—C—P backbone structure ligand represented by Formula 1 below:

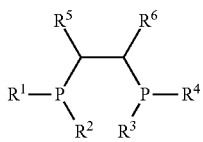

[Formula 1]

wherein $R^1$, $R^2$, $R^3$ and $R^4$, which are arbitrary substituents, are each independently a hydrocarbyl group, a substituted hydrocarbyl group, a heterohydrocarbyl group and a substituted heterohydrocarbyl group adjacent to P atoms, are non-electron donors, and may be nonpolar groups; and preferably $R^1$, $R^2$, $R^3$ and $R^4$ are each independently a substituted aromatic group and a substituted heteroaromatic group, which do not include non-electron donors on atoms adjacent to the atoms bonded with P atoms.

In the P—C—C—P backbone structure ligand represented by Formula 1 above, $R^1$, $R^2$, $R^3$ and $R^4$ may be each independently selected from the group consisting of phenyl, benzyl, naphthyl, anthracenyl, mesityl, xylyl, methyl, ethyl, ethylenyl, propyl, propenyl, propynyl, butyl, cyclohexyl, 4-methylcyclohexyl, 4-ethylcyclohexyl, 4-isopropylcyclohexyl, tolyl, 4-methylphenyl, 4-ethylphenyl, 4-isopropylphenyl, 4-t-butylphenyl, 4-methoxyphenyl, 4-isopropoxyphenyl, cumyl, methoxy, ethoxy, phenoxy, tolyloxy, dimethylamino, thiomethyl, trimethylsilyl, and dimethylhydrazyl. Preferably, $R^1$, $R^2$, $R^3$ and $R^4$ may be each independently selected from the group consisting of phenyl, benzyl, naphthyl, 4-methylphenyl, 4-ethylphenyl, 4-isopropylphenyl, 4-t-butylphenyl, 4-methoxyphenyl, and 4-isopropoxyphenyl.

$R^1$, $R^2$, $R^3$ and $R^4$ may be each independently an aromatic group and a substituted aromatic group, each of the $R^1$, $R^2$, $R^3$ and $R^4$ may be substituted with a non-electron donor group on at least one atom thereof; which is not adjacent to the atom bonded with the P atom, and each of the $R^1$, $R^2$, $R^3$ and $R^4$ may be substituted with a nonpolar group on at least one atom thereof, which is not adjacent to the atom bonded with the P atom.

Further, in the P—C—C—P backbone structure ligand represented by Formula 1 above, $R^5$ and $R^6$ are not hydrogen but each independently a hydrocarbyl group and substituted hydrocarbyl group. Specifically, $R^5$ and $R^6$ may be each independently selected from the group consisting of alkyl, substituted alkyl, aryl, substituted aryl, aryloxy, substituted aryloxy, alkoxycarbonyl, carbonyloxy, alkoxy, aminocarbonyl, carbonylamino, dialkylamino, silyl, derivatives thereof, and aryl substituted with these arbitrary substituents.

The P—C—C—P backbone structure ligand according to the present invention may be a multi P—C—C—P backbone structure ligand, represented by $(R^1)(R^2)P—(R^5)CHCH(R^6)—P(R^3)(R^4)$, in which two or more of the P—C—C—P backbone structure ligands are bonded with each other. This multi P—C—C—P backbone structure ligand includes, but is not limited to, ligands in which dendrimer ligands are bonded with the respective P—C—C—P backbone structure ligand through one or more R groups. Typical examples of such a multi P—C—C—P backbone structure ligand may include 1,2,4,5-tetra-(P(4-ethylphenyl)$_2$)cyclohexane, 1,2,4,5-tetra-(P(4-ethylphenyl)$_2$)benzene, 1,2,3,4-tetra-(P(4-ethylphenyl)$_2$)cyclopentane, and the like.

Examples of the P—C—C—P backbone structure ligand according to the present invention may include, but are not limited to, (phenyl)$_2$P—CH(methyl)CH(methyl)-P(phenyl)$_2$, (4-methoxyphenyl)$_2$P—CH(methyl)CH(methyl)-P(4-methoxyphenyl)$_2$, (4-methylphenyl)$_2$P—CH(methyl)CH(methyl)-P(4-methylphenyl)$_2$, (4-ethylphenyl)$_2$P—CH(methyl)CH(methyl)-P(phenyl)$_2$, (4-ethylphenyl)$_2$P—CH(ethyl)CH(methyl)-P(4-ethylphenyl)$_2$, (4-methoxyphenyl)$_2$P—CH(ethyl)CH(methyl)-P(phenyl)$_2$, (4-ethylphenyl)$_2$P—CH(ethyl)CH(ethyl)-P(4-ethylphenyl)$_2$, (phenyl)$_2$P—CH(ethyl)CH(ethyl)-P(phenyl)$_2$, (phenyl)$_2$P—CH(isopropyl)CH(methyl)-P(phenyl)$_2$, (4-methoxyphenyl)$_2$P—CH(isopropyl)CH(methyl)-P(4-methoxyphenyl)$_2$, (4-ethylphenyl)$_2$P—CH(isopropyl)CH(methyl)-P(4-ethylphenyl)$_2$, (phenyl)$_2$P—CH(n-propyl)CH(methyl)-P(phenyl)$_2$, (4-methoxyphenyl)$_2$P—CH(n-propyl)CH(methyl)-P(4-methoxyphenyl)$_2$, (4-ethylphenyl)$_2$P—CH(n-propyl)CH(methyl)-P(4-ethylphenyl)$_2$, (phenyl)$_2$P—CH(isopropyl)CH(ethyl)-P(phenyl)$_2$, (4-methoxyphenyl)$_2$P—CH(isopropyl)CH(ethyl)-P(4-methoxyphenyl)$_2$, (4-ethylphenyl)$_2$P—CH(isopropyl)CH(ethyl)-P(4-ethylphenyl)$_2$, 1,2-di-(P(phenyl)$_2$)cyclohexane, 1,2-di-(P(4-methoxyphenyl)$_2$)cyclohexane, 1,2-di-(P(4-ethylphenyl)$_2$)cyclohexane, 1,2-di-(P(phenyl)$_2$)cyclopentane, 1,2-di-(P(4-methoxyphenyl)$_2$)cyclopentane, 1,2-di-(P(4-ethylphenyl)$_2$)cyclopentane, 3,4-di-(P(phenyl)$_2$)pyrrole, 3,4-di-(P(4-methoxyphenyl)$_2$)pyrrole, 3,4-di-(P(phenyl)$_2$)pyrrole, 3,4-di-(P(4-methoxyphenyl)$_2$)pyrrole, 3,4-di-(P(4-ethylphenyl)$_2$)pyrrole, 3,4-di-(P(4-ethylphenyl)$_2$)imidazole, (4-ethylphenyl)$_2$P—CH(dimethylamine)CH(dimethylamine)-P(4-ethylphenyl)$_2$, (3-methoxyphenyl)$_2$P—CH(methyl)CH(methyl)-P(3-methoxyphenyl)$_2$, (4-ethoxyphenyl)$_2$P—CH(methyl)CH(methyl)-P(o-ethoxyphenyl)$_2$, (4-dimethylaminephenyl)$_2$P—CH(methyl)CH(methyl)P(4-dimethylaminephenyl)$_2$, and (4-ethylcyclohexyl)$_2$PCH(methyl)CH(methyl)P(4-ethylcyclohexyl)$_2$. The P—C—C—P backbone structure ligand according to the present invention may be prepared using various methods commonly known to those skilled in the art.

The P—C—C—P backbone structure ligand according to the present invention, which is a ligand having an independent structure, unlike a conventional hetero $(R)_nPN(R')P(R)_m$ ligand, has only one hetero atom, phosphorus (P), in the backbone structure thereof. That is, the ligand that is used in the catalyst system of the present invention has two carbon-carbon backbones between two phosphorus atoms, without nitrogen atoms, so that excellent catalytic activity is exhibited and high 1-octene selectivity of 70 wt % or more can be accomplished by suitably adjusting the spatial structure of the ligand by varying the substituents adjacent to the carbon atoms.

In order to prepare 1-octene at high selectivity, a catalyst system comprising the ligand of the present invention may be manufactured through a process of combining transition metal compounds and cocatalysts in an arbitrary order.

The catalyst system according to the present invention may be manufactured through a process of forming a ligand coordination complex using transition metal compounds and the P—C—C—P backbone structure ligand. Here, an in-situ ligand coordination complex having a P—C—C—P backbone structure may also be formed by adding a preformed ligand coordination complex, which is prepared using transition metal compounds and the P—C—C—P backbone structure ligand, to a reaction mixture or by additionally adding transition metal compounds and the P—C—C—P backbone structure ligand to a reactor. The fact that the in-situ ligand coordination complex having a P—C—C—P backbone structure is formed means that the complex is formed in a medium in which a catalytic reaction is conducted. In order to form the in-situ ligand coordination complex, the transition metal compound and the P—C—C—P backbone structure ligand are combined, such that the combination ratio of metal to ligand is about 0.01:1~100:1, preferably about 0.1:1~10:1, and more preferably 0.5:1~2:1. The transition metal that is used for the catalyst system of the present invention may be selected from among chromium, molybdenum, tungsten, titanium, tantalum, vanadium, and zirconium, and may preferably be chromium. The transition metal compound for catalyzing the tetramerization of ethylene according to the present invention may be an inorganic salt, an organic salt, a metal-coordinated complex, or a metallo-organic complex, and may preferably be chromium or a chromium precursor. Here, the chromium or chromium precursor may be selected from the group consisting of chromium(III)acetylacetonate, chromium trichloride tristetrahydrofuran, and chromium(III)2-ethylhexanoate.

The coordination complex of the transition metal compound and the P—C—C—P backbone structure ligand can dissolve at room temperature or higher, but can be transformed to adhere to polymer chains such that it is insoluble. Further, the P—C—C—P backbone structure ligand or the transition metal compound may be fixed by bonding it with silica, silica gel, polysiloxane, alumina, or the like.

The cocatalyst that is used in the present invention may be a compound used to activate a catalyst when it is mixed with the P—C—C—P backbone structure ligand and the transition metal compound. The catalyst activator may be a single compound or a mixture thereof. Preferred examples of the catalyst activator may include organic aluminum compounds, organic boron compounds, and organic salts.

The organic aluminum compound may include a compound, represented by $AlR_3$ (where each R is independently an alkyl group of 1 to 12 carbon atoms, an oxygen-containing alkyl group, or a halide), and a compound, represented by $LiAlH_4$. Examples of the organic aluminum compound may include trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, methylaluminum sesquichloride, and aluminoxane. Aluminoxane is well known in the art as an oligomer compound that can be prepared by mixing an alkylaluminum compound, such as trimethylaluminum, with water. The aluminoxane oligomer compound may be a linear aluminoxane, a cyclic aluminoxane, a cage aluminoxane, or a mixture of two or more different aluminoxanes.

Examples of the organic boron compound may include boroxine, $NaBH_4$, triethylborane, triphenylborane, triphenylborane ammonia complex, tributyl borate, triisopropyl borate, tris(pentafluorophenyl)borane, trityl(tetrapentafluorophenyl)borate, dimethylphenylammonium(tetrapentafluorophenyl)borate, diethylphenylammonium(tetrapentafluorophenyl)borate, methyldiphenylammonium(tetrapentafluorophenyl)borate, ethyldiphenylammonium(tetrapentafluorophenyl)borate, and the like. This organic boron compound may be used in the form in which it is mixed with the organic aluminum compound.

Further, the aluminoxane used as the cocatalyst of the catalyst system according to the present invention may be selected from among alkylaluminoxane, such as methylaluminoxane (MAO) and ethylaluminoxane (EAO), and modified alkylaluminoxane, such as modified methylaluminoxane (MMAO). The modified methylaluminoxane (MMAO), manufactured by Akzo Nobel Corp., includes a hybrid alkyl group, such as an isobutyl group or an n-octyl group, as well as a methyl group.

Aluminoxane may be combined with a transition metal compound, particularly a chromium compound, such that the combination ratio of aluminum to metal is about 1:1~10,000:1, and is preferably about 1:1~1,000:1.

The catalytic components constituting the catalyst system of the present invention may be simultaneously or sequentially combined with each other in the presence of a solvent or in the absence of a solvent. The mixing of the catalytic components may be conducted at a temperature of –20~250° C., and preferably 20~100° C. While the catalytic components are mixed, olefin exhibits a protective effect, thus improving the performance of a catalyst.

The reaction product according to the present invention, that is, 1-hexane, may be prepared through a homogeneous liquid reaction, which is conducted in the presence of an inactive solvent or in the absence of an inactive solvent using a catalyst system, general apparatuses and a conventional contact technology, a slurry reaction, in which part of a catalyst system or all of a catalyst system is not dissolved, a two-phase liquid-liquid reaction, or a bulk phase or gas phase reaction in which olefin acts as a main medium.

When 1-octene is prepared using the catalyst system of the present invention in the presence of an inactive solvent, arbitrary inactive solvents that do not react with each catalytic component and a cocatalyst may be used as the inactive solvent. Such inactive solvents may include saturated aliphatic hydrocarbons, unsaturated aliphatic hydrocarbons, aromatic hydrocarbons and halogenated hydrocarbons, and preferably may include, but are not limited to, benzene, toluene, xylene, cumene, heptane, cyclohexane, methylcyclohexane, methylcyclopentane, n-hexane, 1-hexene, and the like.

The method of preparing 1-octene using the catalyst system of the present invention may be conducted at a temperature of −20~250° C., preferably 15~130° C., and more preferably 30~70° C., and at a reaction pressure of atmospheric pressure to 500 bar, preferably 10~70 bar, and more preferably 30~50 bar.

In the preferred embodiment of the present invention, the P—C—C—P backbone structure ligand coordination complex and reaction conditions are determined such that the yield of 1-octene from ethylene is 30 wt % or more, and preferably 50 wt % or more. In this case, the yield of 1-octene means the weight ratio of 1-octene to total reaction products. Further, in the method of the present invention, in addition to 1-octene, a large or small amount of 1-butene, 1-hexene, methylcyclopentane, methylenecyclopentane and propylcyclopentane, and a large amount of higher oligomers and polyethylene can be prepared, depending on P—C—C—P backbone structure ligand and condition for the reaction.

The method of tetramerizing ethylene according to the present invention may be conducted using a plant equipped with various types of reactors. Examples of the reactors may include, but are not limited to, a batch reactor, a semibatch reactor, and a continuous reactor. The plant may include a reactor, an olefin reactor and a catalyst system inlet port provided in the reactor, a line for discharging oligomerized products from the reactor, and at least one separator for separating the oligomerized products.

1-octene can be produced at high activity and high selectivity while stably maintaining reaction activity by tetramerizing ethylene using the catalyst system of the present invention.

[Mode for Invention]

Hereinafter, the present invention will be described in more detail with reference to the following Examples, which are set forth to illustrate, but are not to be construed as the limit of the present invention.

EXAMPLES

Catalyst Preparation Example 1

Preparation of S,S-(phenyl)$_2$PCH(methyl)CH(methyl)P(phenyl)$_2$ ligand

An S,S-(phenyl)$_2$PCH(methyl)CH(methyl)P(phenyl)$_2$ ligand was prepared as disclosed in the thesis "B. Bosnich et al, J. Am. Chem. Soc. 99(19) (1977) 6262".

(2R,3R)-dibutanediol di-p-toluenesulfonate was prepared from (2R,3R)-dibutanediol. This method of preparing (2R,3R)-dibutanediol di-p-toluenesulfonate was conducted as disclosed in the thesis "R. B. Mitra et al, J. Am. Chem. Soc 84 (1962)". 100 ml (1.24 mol) of dried pyridine was put into a 1 L flask, which is cooled in an ice water bath, and was mixed with 100 g (0.525 mol) of p-toluenesulfonyl chloride, and then 22 ml (0.245 mol) of (2R,3R)-dibutanediol was slowly dropped thereinto to form a mixture. The mixture was heated for 20 minutes until it reached room temperature, and was then left in a semi-solid state at room temperature overnight. Excess ice pieces were added to the mixture, which was then vigorously shaken to prevent agglomeration. After it was observed that powder crystals were slowly separated therefrom, the mixture was stirred for 2 hours together with ice pieces, and then 70 ml of a concentrated hydrochloric acid solution and broken ice pieces were added to this mixture while it was stirred, so as to form a slurry. The slurry thus formed was filtered, water-washed, and then dried to obtain 85 g (86.3%) of (2R,3R)-dibutanediol di-p-toluenesulfonate having a melting point of 62~64° C.

Meanwhile, 95 g of recrystallized triphenylphosphorus and 300 ml of dried tetrahydrofuran (THF) were put into a 1 L three-neck flask equipped with a 250 ml funnel for dropping, a condenser for reflux cooling, and a nitrogen injector to form a solution. 5.0 g of lithium pieces were added to the solution in a nitrogen atmosphere at a temperature of 25° C. with stirring. Thereafter, simultaneously, LiPPh$_2$ was formed in the solution, and heat was generated from the solution, and the solution became dark reddish yellow. The solution was slowly heated for 1 hour to a temperature of 55° C., and was then cooled for 2 hours to a temperature of 25° C., while being stirred. The formed phenyl lithium was decomposed by dropping 33 g of distilled and refined t-butyl chloride thereinto for 45 minutes. The reddish yellow solution was heated for 5 minutes and then cooled to a temperature of −4° C.

Subsequently, 35 g of the obtained (2R,3R)-dibutanediol di-p-toluenesulfonate was dissolved in 100 ml of dried tetrahydrofuran (THF), and then dropped into the reddish yellow solution for 1 hour to form a mixed solution. The mixed solution was slowly heated to room temperature, and was then stirred for 30 minutes. 300 ml of nitrogen-containing water was added to the mixed solution, and then tetrahydrofuran (THF) was removed therefrom through vacuum distillation, thereby extracting a colorless oily product therefrom. The oily product was extracted twice using 150 ml of ether, and was then dried using Na$_2$SO$_4$ to form an ether extract. The ether extract was filtered in a solution of 50 ml of ethanol and 15 g of nickel perchlorate hexahydrate in a nitrogen atmosphere. Na$_2$SO$_4$ remaining in the filtered ether extract was completely washed to form an ether solution, and then the ether solution was added to a nickel solution. As a result, a reddish brown oily product having yellow crystals, [Ni((S,S)-chiraphos)$_2$](ClO$_4$)$_2$, was formed. This oily crystalline mixture was added to a solution in which 15 g of sodium thiocyanate is dissolved in 50 mL of ethanol to form a mixture solution, and then the mixture solution was vigorously stirred for several hours to form a yellowish brown solid product, [Ni((S,S)-chiraphos)$_2$NCS]NCS. This solid product was completely washed with ethanol and was then finally washed with ether to form a nickel complex.

15 g of this nickel complex was floated with 150 ml of ethanol in a nitrogen atmosphere, and was then stirred and heated. 20 g of water and 4 g of sodium cyanate (NaCN) were added to the nickel complex. Thus, the nickel complex was slowly dissolved, and was thus formed into a red solution, [Ni((S,S)-chiraphos)$_2$CN$_3$]$^-$, and then the red solution changed into a turbid beige solution. The turbid solution was stirred to form a yellow slurry solution. The slurry solution was cooled to be formed into a solid, and then the solid was washed twice with 25 ml of water and then rapidly cooled using ethanol cooled by ice to form a beige solid containing impurities. The beige solid containing impurities was dried at a temperature of 25° C., was added to 125 ml of anhydrous ethanol, and was then filtered using a Fritz filter at room temperature for 12 hours. As a result, only a colorless glossy solid remained. Finally, the colorless glossy solid was recrystallized using 60 ml of anhydrous ethanol to obtain 5.5 g of colorless pure S,S-(phenyl)$_2$PCH(methyl)CH(methyl)P(phenyl)$_2$.

Example 1

Tetramerization of ethylene using Cr(III)(acetylacetonate)$_3$, (phenyl)$_2$PCH(methyl)CH(methyl)P(phenyl)$_2$ and MAO 100 ml of cyclohexane and 4.0 mmol-Al of MAO were put into a 300 ml stainless steel reactor, which had been washed in nitrogen or in a vacuum, and were then heated to a temperature of 45° C. 3.5 mg (0.010 mmol) of Cr(III)(acetylacetonate)$_3$ in 10 ml of toluene was put into a 50 ml Schlenk flask in a glove box and then mixed with 4.3 mg (0.010 mmol) of (phenyl)$_2$PCH(methyl)CH(methyl)P(phenyl)$_2$, obtained in Catalyst Preparation Example 1, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then weighed to obtain 3.6 g of polyethylene. Further, it was found that the total weight of the reaction mixture, determined through GC, was 101.6 g. The product distribution of this Example is given in Table 1.

Example 2

Tetramerization of ethylene using Cr(III)(acetylacetonate)$_3$, (phenyl)$_2$PCH(methyl)CH(methyl)P(phenyl)$_2$ and MAO 100 ml of cyclohexane and 2.0 mmol-Al of MAO were put into the 300 ml stainless steel reactor of Example 1, which had been washed in nitrogen or in a vacuum, and were then heated to a temperature of 45° C. 0.7 mg (0.002 mmol) of Cr(III)(acetylacetonate)$_3$ in 10 ml of toluene was put into a 50 ml Schlenk flask in a glove box and then mixed with 0.86 m (0.002 mmol) of (phenyl)$_2$PCH(methyl)CH(methyl)P(phenyl)$_2$, obtained in Catalyst Preparation Example 1, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 18.0 g. The product distribution of this Example is given in Table 1.

Example 3

Tetramerization of ethylene using CrCl$_3$(tetrahydrofuran)$_3$, (phenyl)$_2$PCH(methyl)CH(methyl)P(phenyl)$_2$ and MAO 100 ml of cyclohexane and 4.0 mmol-Al of MAO were put into the 300 ml stainless steel reactor of Example 1, which had been washed in nitrogen or in a vacuum, and were then heated to a temperature of 45° C. 3.75 mg (0.01 mmol) of CrCl$_3$(tetrahydrofuran)$_3$ in 10 ml of toluene was put into a 50 ml Schlenk flask in a glove box and then mixed with 4.3 mg (0.01 mmol) of (phenyl)$_2$PCH(methyl)CH(methyl)P(phenyl)$_2$, obtained in Catalyst Preparation Example 1, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 36.2 g. The product distribution of this Example is given in Table 1.

Example 4

Tetramerization of ethylene using Cr(2-ethylhexanoate)$_3$, (phenyl)$_2$PCH(methyl)CH(methyl)P(phenyl)$_2$ and MAO 100 ml of cyclohexane and 4.0 mmol-Al of MAO were put into the 300 ml stainless steel reactor of Example 1, which had been washed in nitrogen or in a vacuum, and were then heated to a temperature of 45° C. 4.0 mg (0.01 mmol) of Cr(2-ethylhexanoate)$_3$ in 10 ml of toluene was put into a 50 ml Schlenk flask in a glove box and then mixed with 4.3 mg(0.01 mmol) of (phenyl)$_2$PCH(methyl)CH(methyl)P(phenyl)$_2$, obtained in Catalyst Preparation Example 1, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 76.0 g. The product distribution of this Example is given in Table 1.

Example 5

Tetramerization of ethylene using Cr(2-ethylhexanoate)$_3$, (phenyl)$_2$PCH(methyl)CH(methyl)P(phenyl)$_2$ and MAO 100 ml of cyclohexane and 2.0 mmol-Al of MAO were put into the 300 ml stainless steel reactor of Example 1, which had been washed in nitrogen or in a vacuum, and were then heated to a temperature of 45° C. 0.8 mg (0.002 mmol) of Cr(2-ethylhexanoate)$_3$ in 10 ml of toluene was put into a 50 ml Schlenk flask in a glove box and then mixed with 0.86 mg (0.002 mmol) of (phenyl)$_2$PCH(methyl)CH(methyl)P(phenyl)$_2$, obtained in Catalyst Preparation Example 1, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 11.2 g. The product distribution of this Example is given in Table 1.

Catalyst Preparation Example 2

Preparation of R,R-(4-methoxyphenyl)2P—CH(methyl)CH(methyl)-P(4-methoxyphenyl)$_2$ ligand An R,R-(4-methoxyphenyl)$_2$P—CH(methyl)CH(methyl)-P(4-methoxyphenyl)$_2$ ligand was prepared as disclosed in the thesis "B. Bosnich et al, J. Am. Chem. Soc. 99(19) (1977) 6262".

The preparation of (2R,3R)-dibutanediol di-p-toluenesulfonate from (2R,3R)-dibutanediol was conducted using the same method as in Catalyst Preparation Example 1.

The preparation of tri(4-methoxyphenyl)phosphorus was conducted as follows. Magnesium pieces (91.1 g, 3.75 mol) were dropped into 95 ml (0.75 mol) of 4-bromo-anisole in 2 L of tetrahydrofuran (THF). The mixture reacted strongly, and was then refluxed and heated for 2 hours to obtain a Grignard reagent. This Grignard reagent was dropped into 17.5 ml (0.2 mol) of a PCl$_3$ solution in 2 L of tetrahydrofuran (THF) at a temperature of −78° C. for 2 hours, while being stirred therein. Thereafter, dry ice and acetone were removed from the reaction product, and then the reaction product was heated to room temperature. The reaction product was stirred overnight, and then the solvent was removed therefrom in a vacuum to form phosphine. The entire reaction product was used in subsequent processes, without removing the phosphine therefrom.

Meanwhile, 70 g of recrystallized tri(4-methoxyphenyl)phosphorus and 300 ml of dried tetrahydrofuran (THF) were put into a 1 L three-neck flask equipped with a 250 ml funnel for dropping, a condenser for reflux cooling and a nitrogen injector to form a solution. 2.8 g of lithium pieces were added to the solution in a nitrogen atmosphere at a temperature of 25° C. with stirring. Thereafter, simultaneously, LiP(4-OMe-Ph)$_2$ was formed in the solution, heat was generated in the solution, and the solution became dark reddish yellow. The solution was slowly heated for 1 hour to a temperature of 55° C. and was then cooled for 2 hours to a temperature of 25° C., while being stirred. The 4-methoxyphenyllithium thus formed was decomposed by dropping 18.5 g of distilled and refined t-butyl chloride thereinto for 45 minutes. The reddish yellow solution was heated for 5 minutes and then cooled to a temperature of −4° C.

Subsequently, 19.6 g of the (2R,3R)-dibutanediol di-p-toluenesulfonate thus obtained was dissolved in 100 ml of dried tetrahydrofuran (THF), and was then dropped into the reddish yellow solution over 1 hour to form a mixed solution. The mixed solution was slowly heated to room temperature and then stirred for 30 minutes. 300 ml of nitrogen-containing water was added to the mixed solution, and then tetrahydrofuran (THF) was removed therefrom through vacuum distillation, thereby extracting a colorless oily product therefrom. The oily product was extracted twice using 150 ml of ether, and was then dried by Na$_2$SO$_4$ to form an ether extract. The ether extract was filtered in a solution of 50 ml of ethanol and 8.4 g of nickel perchlorate hexahydrate in a nitrogen atmosphere. Na$_2$SO$_4$ remaining in the filtered ether extract was completely washed to form an ether solution, and then the ether solution was added to a nickel solution. As a result, a reddish brown oily product having yellow crystals, [Ni((2S,3S)-bis(di-p-methoxyphenyl)phosphorous butane)$_2$](ClO$_4$)$_2$, was formed. This oily crystalline mixture was added to a solution in which 8.4 g of sodium thiocyanate is dissolved in 50 mL of ethanol to form a mixture solution, and then the mixture solution was vigorously stirred for several hours to form a yellowish brown solid product, [Ni((2S,3S)-bis(di-p-methoxyphenyl)phosphorous butane)$_2$NCS]NCS. This solid product was completely washed with ethanol and was then finally washed with ether to form a nickel complex.

17 g of this nickel complex was floated with 150 ml of ethanol in a nitrogen atmosphere, and was then stirred and heated. 20 g of water and 4 g of sodium cyanate (NaCN) were added to the nickel complex. Thus, the nickel complex was slowly dissolved, and was thus formed into a red solution, [Ni((2S,3S)-bis(di-p-methoxyphenyl)phosphorous butane)$_2$CN$_3$]$^-$, and then the red solution was changed into a turbid beige solution. The turbid solution was stirred to form a yellow slurry solution. The slurry solution was cooled to form it into a solid, and then the solid was washed with 25 ml of water twice and then rapidly cooled using ethanol, cooled using ice, to form a beige solid containing impurities. The beige solid containing impurities was dried at a temperature of 25° C., was added to 125 ml of boiling anhydrous ethanol, and was then filtered using a Fritz filter at room temperature for 12 hours. As a result, only a colorless glossy solid remained. Finally, the colorless glossy solid was recrystallized using 60 ml of anhydrous ethanol to obtain 6.2 g of colorless pure S,S-(4-methoxyphenyl)$_2$PCH(methyl)CH(methyl)P(4-methoxyphenyl)$_2$.

Example 6

Tetramerization of ethylene using Cr(III)(acetylacetonate)$_3$, R,R-(4-methoxyphenyl)$_2$P—CH(methyl)CH(methyl)-P(4-methoxyphenyl)$_2$ and MAO 100 ml of cyclohexane and 4.0 mmol-Al of MAO were put into the 300 ml stainless steel reactor of Example 1, which had been washed in nitrogen or in a vacuum, and were then heated to a temperature of 45° C. 3.5 mg (0.010 mmol) of Cr(III)(acetylacetonate)$_3$ in 10 ml of toluene was put into a 50 ml in Schlenk flask in a glove box and then mixed with 5.5 mg (0.010 mmol) of R,R-(4-methoxyphenyl)$_2$P—CH(methyl)CH(methyl)-P(4-methoxyphenyl)$_2$, obtained in Catalyst Preparation Example 2, to form a mixture, and then the mixture was stirred at room temperature for 5 minutes and then added to the reactor. Subsequently, ethylene was charged in the reactor at a pressure of 30 bar, and was then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then weighed to obtain 1.9 g of polyethylene. Further, it was found that the total weight of the reaction mixture, determined through GC, was 45.5 g. The product distribution of this Example is given in Table 1.

Example 7

Tetramerization of ethylene using CrCl$_3$(tetrahydrofuran)$_3$, R,R-(4-methoxyphenyl)$_2$P—CH(methyl)CH(methyl)-P(4-methoxyphenyl)$_2$ and MAO 100 ml of cyclohexane and 4.0 mmol-Al of MAO were put into the 300 ml stainless steel reactor of Example 1, which had been washed in nitrogen or in a vacuum, and were then heated to a temperature of 45° C. 3.75 mg (0.01 mmol) of CrCl$_3$(tetrahydrofuran)$_3$ in 10 ml of toluene was put into a 50 ml Schlenk flask in a glove box and then mixed with 5.5 mg (0.010 mmol) of R,R-(4-methoxyphenyl)$_2$P—CH(methyl)CH(methyl)-P(4-methoxyphenyl)$_2$, obtained in Catalyst Preparation Example 2, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 25.3 g. The product distribution of this Example is given in Table 1.

Example 8

Tetramerization of ethylene using Cr(2-ethylhexanoate)$_3$, R,R-(4-methoxyphenyl)$_2$P—CH(methyl)CH(methyl)-P(4-methoxyphenyl)$_2$ and MAO 100 ml of cyclohexane and 4.0 mmol-Al of MAO were put into the 300 ml stainless steel reactor of Example 1, which had been washed in nitrogen or in a vacuum, and were then heated to a temperature of 45° C. 4.0 mg (0.01 mmol) of Cr(2-ethylhexanoate)$_3$ in 10 ml of toluene was put into a 50 ml Schlenk flask in a glove box and then mixed with 5.5 mg (0.010 mmol) of R,R-(4-methoxyphenyl)$_2$P—CH(methyl)CH(methyl)-P(4-methoxyphenyl)$_2$, obtained in Catalyst Preparation Example 2, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 48.2 g. The product distribution of this Example is given in Table 1.

Comparative Catalyst Preparation Example 1

Preparation of (phenyl)$_2$PN(isopropyl)P(phenyl)$_2$ ligand

A mixed heteroatomic PNP ligand was prepared by reacting amine with phosphine chloride (R$_2$PCl), as disclosed in the theses: (a) "Ewart et al, J. Chem. Soc. 1964, 1543"; (b) "Dossett, S. J. et. al, Chem. Commun., 2001, 8, 699"; and (c) "Balakrishna, M. S. et al, J. Organomet. Chem. 1990, 390, 2, 203". Further, reactive phosphine chloride (R$_2$PCl) was prepared as disclosed in the theses: "Casalnuovo, A. L. et al, J. Am. Chem. Soc. 1994, 116, 22, 9869"; and "Rajanbabu, T. V. et al, J. Org. Chem. 1997, 62, 17, 6012".

15 ml of triethylamine and 28 mmol of chlorodiphenyl phosphine were dissolved in 80 ml of DMC, and then 1.11 ml (13 mmol) of isopropylamine was added thereto. The reaction mixture was stirred for 30 minutes, and then impurities were removed therefrom. The reaction mixture was further stirred for 24 hours, and was then filtered to remove triethylammonium salts therefrom. The product was crystallized, and then separated to obtain a (phenyl)$_2$PN(isopropyl)P(phenyl)$_2$ ligand at a yield of 85%.

Comparative Example 1

Tetramerization of ethylene using Cr(III)(acetylacetonate)$_3$, (phenyl)-$_2$PN(isopropyl)P(phenyl)$_2$ and MAO 100 ml of cyclohexane and 3.0 mmol-Al of MAO were put into the 300 ml stainless steel reactor of Example 1, which had been washed in nitrogen or in a vacuum, and were then heated to a temperature of 45° C. 5.2 mg (0.015 mmol) of Cr(III)(acetylacetonate)$_3$ in 10 ml of toluene was put into a 50 ml Schlenk flask in a glove box and then mixed with 6.4 mg (0.015 mmol) of (phenyl)$_2$PN(isopropyl)P(phenyl)$_2$, obtained in Comparative Catalyst Preparation Example 1, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 32.2 g. The product distribution of this Example is given in Table 1.

Comparative Example 2

Tetramerization of ethylene using Cr(III)(2-ethylhexanoate)$_3$, (phenyl)$_2$PN(isopropyl)P(phenyl)$_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 5.2 mg (0.015 mmol) of Cr(III)(2-ethylhexanoate)$_3$ in 10 ml of toluene was put into a 50 ml Schlenk flask in a glove box and then mixed with 6.4 mg (0.015 mmol) of (phenyl)$_2$PN(isopropyl)P(phenyl)$_2$, obtained in Comparative Catalyst Preparation Example 1, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 70.0 g. The product distribution of this Example is given in Table 1.

Comparative Catalyst Preparation Example 2

Preparation of (phenyl)$_2$PCH$_2$P(phenyl)$_2$ ligand

A (phenyl)$_2$PCH$_2$P(phenyl)$_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N-dimethylformamide suspension mixed with 1.0 g of activated molecular sieve powder having a particle size of 4 Å, and then stirred in a nitrogen atmosphere. Subsequently, 0.38 ml (2.14 mmol) of diphenyl phosphine added thereto, and then stirred at room temperature for 1 hour to form a dark reddish orange solution. 0.09 ml (1.29 mmol) of dimethylbromide dropped into the solution, which thus became white. The solution was reacted for 16 hours at room temperature, and 60 ml of distilled water was added thereto, and the solution was extracted three times using 60 ml of DMC to form an organic layer. The organic layer was washed three times with distilled water, and was dried using anhydrous sodium sulfate, a solvent was removed therefrom in a vacuum, and then the organic layer, from which the solvent had been removed, was recrystallized in a benzene solvent, thereby obtaining air-sensitive white crystals (390 mg, yield 95%).

Comparative Example 3

Tetramerization of ethylene using Cr(III)(acetylacetonate)$_3$, (phenyl)$_2$PCH$_2$P(phenyl)$_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 10.5 mg (0.03 mmol) of Cr(III)(acetylacetonate)$_3$ in 10 ml of toluene was put into a 50 ml Schlenk flask in a glove box and then mixed with 11.5 mg (0.03 mmol) of (phenyl)$_2$PCH$_2$P(phenyl)$_2$, obtained in Comparative Catalyst Preparation Example 2, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 1.47 g. The product distribution of this Example is given in Table 1.

Comparative Catalyst Preparation Example 3

Preparation of (phenyl)$_2$PCH$_2$CH$_2$P(phenyl)$_2$ ligand

A (phenyl)$_2$PCH$_2$P(phenyl)$_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N-dimethylformamide suspension mixed with 1.0 g of activated molecular sieve powder having a particle size of 4 Å, and was then stirred in a nitrogen atmosphere. Subsequently, 0.38 ml (2.14 mmol) of diphenyl phosphine was added thereto, and was then stirred at room temperature for 1 hour to form a dark reddish orange solution. 0.11 ml (1.29 mmol) of 1,2-dibromoethane was dropped into the solution, which thus became white. The solution was reacted for 36 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (333 mg, yield 78%).

Comparative Example 4

Tetramerization of ethylene using Cr(III)(acetylacetonate)$_3$, (phenyl)$_2$PCH$_2$CH$_2$P(phenyl)$_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 5.2 mg (0.015 mmol) of Cr(III)(acetylacetonate)$_3$ in 10 ml of toluene was put into a 50 ml Schlenk flask in a glove box and then mixed with 7.8 mg (0.02 mmol) of (phenyl)$_2$PCH$_2$CH$_2$P(phenyl)$_2$, obtained in Comparative Catalyst Preparation Example 3, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 10.4 g. The product distribution of this Example is given in Table 1.

Comparative Catalyst Preparation Example 4

Preparation of (phenyl)$_2$P(CH$_2$)$_3$P(phenyl)$_2$ ligand

A (phenyl)$_2$P(CH$_2$)$_3$P(phenyl)$_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N-dimethylformamide suspension mixed with 1.0 g of activated molecular sieve powder having a particle size of 4 Å, and was then stirred in a nitrogen atmosphere. Subsequently, 0.38 ml (2.14 mmol) of diphenyl phosphine was added thereto, and was then stirred at room temperature for 1 hour to form a dark reddish orange solution. 0.13 ml (1.29 mmol) of 1,2-dibromopropane was dropped into the solution, which thus became white. The solution was reacted for 45 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (366 mg, yield 83%).

Comparative Example 5

Tetramerization of ethylene using Cr(III)(acetylacetonate)$_3$, (phenyl)$_2$P(CH$_2$)$_3$P(phenyl)$_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 9.6 mg (0.028 mmol) of Cr(III)(acetylacetonate)$_3$ in 10 ml of toluene was put into a 50 ml Schlenk flask in a glove box and then mixed with 13.8 mg (0.033 mmol) of (phenyl)$_2$P(CH$_2$)$_3$P(phenyl)$_2$, obtained in Comparative Catalyst Preparation Example 4, to form a mixture, and then the mixture was stirred at room temperature for 5 minutes and then added to the reactor. Subsequently, ethylene was charged in the reactor at a pressure of 30 bar, and was then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 28.8 g. The product distribution of this Example is given in Table 1.

Comparative Catalyst Preparation Example 5

Preparation of (phenyl)$_2$P(CH$_2$)$_4$P(phenyl)$_2$ ligand

A (phenyl)$_2$P(CH$_2$)$_4$P(phenyl)$_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N-dimethylformamide suspension mixed with 1.0 g of activated molecular sieve powder having a particle size of 4 Å, and was then stirred in a nitrogen atmosphere. Subsequently, 0.38 ml (2.14 mmol) of diphenyl phosphine was added thereto, and was then stirred at room temperature for 1 hour to form a dark reddish orange solution. 0.16 ml (1.29 mmol) of 1,2-dibromobutane was dropped into the solution, which thus became white. The solution was reacted for 48 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (397 mg, yield 87%).

Comparative Example 6

Tetramerization of ethylene using $Cr(III)(acetylacetonate)_3$, $(phenyl)_2P(CH_2)_4P(phenyl)_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 9.7 mg (0.028 mmol) of $Cr(III)(acetylacetonate)_3$ in 10 ml of toluene was put into a 50 ml Schlenk flask in a glove box and then mixed with 15.4 mg (0.036 mmol) of $(phenyl)_2P(CH_2)_4P(phenyl)_2$, obtained in Comparative Catalyst Preparation Example 5, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 18.5 g. The product distribution of this Example is given in Table 1.

Comparative Catalyst Preparation Example 6

Preparation of $(phenyl)_2P(CH=CH)P(phenyl)_2$ ligand

A $(phenyl)_2P(CH=CH)P(phenyl)_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N-dimethylformamide suspension mixed with 1.0 g of activated molecular sieve powder having a particle size of 4 Å, and was then stirred in a nitrogen atmosphere. Subsequently, 0.38 ml (2.14 mmol) of diphenyl phosphine was added thereto, and was then stirred at room temperature for 1 hour to form a dark reddish orange solution. 0.11 ml (1.29 mmol) of 1,2-dibromoethylene was dropped into the solution, which thus became white. The solution was reacted for 48 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (284 mg, yield 67%).

Comparative Example 7

Tetramerization of ethylene using $Cr(III)(acetylacetonate)_3$, $(phenyl)_2P(CH=CH)P(phenyl)_2$ and MAO 100 ml of cyclohexane and 9.0 mmol-Al of MAO were put into the 300 ml stainless steel reactor of Example 1, which had been washed in nitrogen or in a vacuum, and were then heated to a temperature of 45° C. 10.5 mg (0.03 mmol) of $Cr(III)(acetylacetonate)_3$ in 10 ml of toluene was put into a 50 ml Schlenk flask in a glove box and then mixed with 23.8 mg (0.06 mmol) of $(phenyl)_2P(CH=CH)P(phenyl)_2$, obtained in Comparative Catalyst Preparation Example 6, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 1.3 g. The product distribution of this Example is given in Table 1.

Comparative Catalyst Preparation Example 7

Preparation of $(phenyl)_2P(1,2-phenyl)P(phenyl)_2$ ligand

A $(phenyl)_2P(1,2-phenyl)P(phenyl)_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 in of an anhydrous N,N-dimethylformamide suspension mixed with 1.0 g of activated molecular sieve powder having a particle size of 4 Å, and was then stirred in a nitrogen atmosphere. Subsequently, 0.38 ml (2.14 mmol) of diphenyl phosphine was added thereto, and was then stirred at room temperature for 1 hour to form a dark reddish orange solution. 0.16 ml (1.29 mmol) of 1,2-dibromobenzene was dropped into the solution, which thus became white. The solution was reacted for 60 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (358 mg, yield 75%).

Comparative Example 8

Tetramerization of ethylene using Cr(III)(acetylacetonate)$_3$, (phenyl)$_2$P(1,2-phenyl)P(phenyl)$_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 10.5 mg (0.03 mmol) of Cr(III)(acetylacetonate)$_3$ in 10 ml of toluene was put into a 50 ml Schlenk flask in a glove box and then mixed with 21.8 mg (0.049 mmol) of (phenyl)$_2$P(1,2-phenyl)P(phenyl)$_2$, obtained in Comparative Catalyst Preparation Example 7, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 19.6 g. The product distribution of this Example is given in Table 1.

Comparative Catalyst Preparation Example 8

Preparation of (cyclohexyl)$_2$PCH$_2$P(cyclohexyl)$_2$ ligand

A (cyclohexyl)$_2$PCH$_2$P(cyclohexyl)$_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N-dimethylformamide suspension mixed with 1.0 g of activated molecular sieve powder having a particle size of 4 Å, and was then stirred in a nitrogen atmosphere. Subsequently, 0.43 ml (2.14 mmol) of dicyclohexyl phosphine was added thereto, and was then stirred at room temperature for 1 hour to form a dark reddish orange solution. 0.09 ml (1.29 mmol) of dibromomethane was dropped into the solution, which thus became white. The solution was reacted for 38 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (372 mg, yield 85%).

Comparative Example 9

Tetramerization of ethylene using Cr(III)(acetylacetonate)$_3$, (cyclohexyl)$_2$PCH$_2$P(cyclohexyl)$_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 10.5 mg (0.03 mmol) of Cr(III)(acetylacetonate)$_3$ in 10 ml of toluene was put into a 50 ml Schlenk flask in a glove box and then mixed with 12.2 mg (0.03 mmol) of (cyclohexyl)$_2$PCH$_2$P(cyclohexyl)$_2$, obtained in Comparative Catalyst Preparation Example 8, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 9.4 g. The product distribution of this Example is given in Table 1.

Comparative Catalyst Preparation Example 9

Preparation of (cyclohexyl)$_2$PCH$_2$CH$_2$P(cyclohexyl)$_2$ ligand

A (cyclohexyl)$_2$PCH$_2$CH$_2$P(cyclohexyl)$_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N- dimethylformamide suspension mixed with 1.0 g of activated molecular sieve powder having a particle size of 4 Å, and was then stirred in a nitrogen atmosphere. Subsequently, 0.43 ml (2.14 mmol) of dicyclohexyl phosphine was added thereto, and was then stirred at room temperature for 1 hour to form a dark reddish orange solution. 0.11 (1.29 mmol) of 1,2-dibromoethane was dropped into the solution, which thus became white. The solution was reacted for 49 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (366 mg, yield 81%).

Comparative Example 10

Tetramerization of ethylene using $Cr(III)(acetylacetonate)_3$, $(cyclohexyl)_2PCH_2CH_2P(cyclohexyl)_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 10.5 mg (0.03 mmol) of $Cr(III)(acetylacetonate)_3$ in 10 ml of toluene was put into a 50 ml Schlenk flask in a glove box and then mixed with 12.7 mg (0.03 mmol) of $(cyclohexyl)_2PCH_2CH_2P(cyclohexyl)_2$, obtained in Comparative Catalyst Preparation Example 9, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 2.2 g. The product distribution of this Example is given in Table 1.

Comparative Catalyst Preparation Example 10

Preparation of $(ethyl)_2PCH_2CH_2P(ethyl)_2$ ligand

A $(ethyl)_2PCH_2CH_2P(ethyl)_2$ ligand was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N-dimethylformamide suspension mixed with 1.0 g of activated molecular sieve powder having a particle size of 4 Å, and was then stirred in a nitrogen atmosphere. Subsequently, 0.25 ml (2.14 mmol) of diethyl phosphine was added thereto, and was then stirred at room temperature for 1 hour to form a dark reddish orange solution. 0.11 ml (1.29 mmol) of 1,2-dibromoethane was dropped into the solution, which thus became white. The solution was reacted for 72 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (126 mg, yield 57%).

Comparative Example 11

Tetramerization of ethylene using $Cr(III)(acetylacetonate)_3$, $(ethyl)_2PCH_2CH_2P(ethyl)_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 5.4 mg (0.016 mmol) of $Cr(III)(acetylacetonate)_3$ in 10 ml of toluene was put into a 50 ml Schlenk flask in a glove box and then mixed with 3.3 mg (0.016 mmol) of $(ethyl)_2PCH_2CH_2P(ethyl)_2$, obtained in Comparative Catalyst Preparation Example 10, to form a mixture, and then the mixture was stirred at room temperature for 5 minutes and then added to the reactor. Subsequently, ethylene was charged in the reactor at a pressure of 30 bar, and was then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 2.7 g. The product distribution of this Example is given in Table 1.

Comparative Catalyst Preparation Example 11

Preparation of $(phenyl)_2PCH(methyl)CH_2P(phenyl)_2$ ligand

A $(phenyl)_2PCH(methyl)CH_2P(phenyl)_2$ was prepared by reacting diphenylphosphine with 2 equivalents of dibromoalkyl in dimethylfluoromethylene (DMF) and cesium hydroxide atmospheres, as disclosed in the document "R. N. Salvatore et al, Tetrahedron Letters 44 (2003) 8373". First, 360 mg (2.14 mmol) of a cesium hydroxide monohydrate was added to 16.6 ml of an anhydrous N,N-dimethylformamide suspension mixed with 1.0 g of activated molecular sieve powder having a particle size of 4 Å, and was then stirred in a nitrogen atmosphere. Subsequently, 0.38 ml (2.14 mmol) of diphenyl phosphine was added thereto, and was then stirred at room temperature for 1 hour to form a dark reddish orange solution. 0.14 ml (1.3 mmol) of 1,2-dibromopropane was dropped into the solution, which thus became white. The solution was reacted for 72 hours at room temperature, and 60 ml of distilled water was added thereto, and the solution was extracted three times using 60 ml of DMC to form an organic layer. The organic layer was washed three times with distilled water, and was dried using anhydrous sodium sulfate, the solvent was removed therefrom in a vacuum, and then the organic layer, from which the solvent had been removed, was recrystallized in a benzene solvent, thereby obtaining air-sensitive white crystals (309 mg, yield 70%).

Comparative Example 12

Tetramerization of ethylene using Cr(III)(acetylacetonate)$_3$, (phenyl)$_2$PCH(methyl)CH$_2$P(phenyl)$_2$ and MAO 100 ml of cyclohexane and 6.0 mmol-Al of MAO were put into the 300 ml stainless steel reactor of Example 1, which had been washed in nitrogen or in a vacuum, and were then heated to a temperature of 45° C. 1.7 mg (0.005 mmol) of Cr(III)(acetylacetonate)$_3$ in 10 ml of toluene was put into a 50 ml Schlenk flask in a glove box and then mixed with 2.1 mg (0.005 mmol) of (phenyl)$_2$PCH(methyl)CH$_2$P(phenyl)$_2$, obtained in Comparative Catalyst Preparation Example 11, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 4.8 g. The product distribution of this Example is given in Table 1.

Comparative Example 13

Tetramerization of ethylene using Cr(III)(acetylacetonate)$_3$, (phenyl)$_2$PCH(methyl)CH$_2$P(phenyl)$_2$ and MAO 100 ml of cyclohexane and 4.0 mmol-Al of MAO were put into the 300 ml stainless steel reactor of Example 1, which had been washed in nitrogen or in a vacuum, and were then heated to a temperature of 45° C. 3.4 mg (0.010 mmol) of Cr(III)(acetylacetonate)$_3$ in 10 mi of toluene was put into a 50 ml Schlenk flask in a glove box and then mixed with 4.2 mg (0.010 mmol) of (phenyl)$_2$PCH(methyl)CH$_2$P(phenyl)$_2$, obtained in Comparative Catalyst Preparation Example 11, to form a mixture, and then the mixture was stirred at room temperature for 5 minutes and then added to the reactor. Subsequently, ethylene was charged in the reactor at a pressure of 30 bar, and then stirred at a stirring speed of 600 rpm. After 30 minutes, the supply of ethylene and the stirring thereof were stopped, and the reactor was cooled to a temperature of less than 10° C.

Subsequently, excess ethylene was discharged from the reactor, and then ethanol mixed with 10 vol % of hydrochloric acid was added to the liquid present in the reactor. In order to analyze the liquid using GC-FID, nonane, serving as an internal standard substance, was added thereto. Some organic layer samples were passed through anhydrous magnesium sulfate, dried, and then analyzed using GC-FID. Other organic layer samples were filtered, and then a solid wax/polymer product was separated therefrom. This solid product was dried in an oven at a temperature of 100° C. overnight, and was then analyzed using GC. It was found that the weight of the product, determined through GC, was 6.0 g. The product distribution of this Example is given in Table 1.

TABLE 1

Results of tetramerization of ethylene

| | Product (g) | Activity (Kg/g-Cr) | 1-C6 (%) | 1-C8 (%) | Others (%) | Polymer (%) |
|---|---|---|---|---|---|---|
| Exp. 1 | 38.2 | 75.2 | 18.5 | 67.9 | 10.1 | 3.5 |
| Exp. 2 | 18.0 | 168.3 | 17.0 | 68.0 | 10.6 | 4.4 |
| Exp. 3 | 30.5 | 60.2 | 18.5 | 61.5 | 14.8 | 5.1 |
| Exp. 4 | 35.0 | 68.5 | 13.1 | 72.7 | 11.6 | 2.6 |
| Exp. 5 | 11.2 | 107.6 | 16.7 | 69.5 | 10.5 | 3.4 |
| Exp. 6 | 45.5 | 87.5 | 15.0 | 66.3 | 14.5 | 4.2 |
| Exp. 7 | 25.3 | 48.7 | 14.5 | 63.3 | 17.9 | 4.3 |
| Exp. 8 | 48.2 | 92.7 | 13.7 | 72.9 | 11.7 | 1.7 |
| Co. Exp 1 | 32.2 | 40.8 | 20.3 | 64.6 | 7.7 | 4.7 |
| Co. Exp 2 | 32.0 | 40.0 | 26.0 | 58.0 | 12.9 | 2.9 |
| Co. Exp 3 | 1.47 | 0.94 | 1.0 | 3.8 | 11.4 | 83.6 |
| Co. Exp 4 | 10.4 | 14.0 | 8.5 | 27.4 | 14.8 | 42.7 |
| Co. Exp 5 | 28.8 | 20.2 | 10.9 | 9.0 | 48.3 | 30.9 |
| Co. Exp 6 | 18.5 | 12.8 | 8.5 | 8.6 | 27.9 | 56.2 |
| Co. Exp 7 | 1.3 | 0.8 | 3.1 | 46.2 | 35.6 | 23.1 |
| Co. Exp 8 | 19.5 | 12.5 | 15.3 | 52.0 | 23.5 | 9.2 |
| Co. Exp 9 | 9.4 | 6.1 | 9.1 | 48.4 | 25.3 | 17.1 |
| Co. Exp 10 | 2.2 | 1.4 | 12.8 | 2.7 | 16.0 | 68.6 |
| Co. Exp 11 | 2.7 | 3.3 | 7.4 | 20.4 | 37.1 | 35.0 |
| Co. Exp 12 | 4.8 | 17.9 | 3.4 | 9.8 | 6.9 | 79.9 |
| Co. Exp 13 | 6.0 | 11.3 | 8.3 | 47.8 | 25.6 | 18.3 |

Examples 9 to 12

Changes in reaction activity and selectivity depending on reaction time in the tetramerization of ethylene using Cr(III)(acetylacetonate)$_3$, (phenyl)$_2$PCH (methyl)CH(methyl)P(phenyl)$_2$ and MMAO-12

The tetramerization of ethylene was conducted using 1.75 mg (0.005 mmol) of Cr(III)(acetylacetonate)$_3$, 2.2 mg (0.005 mmol) of (phenyl)$_2$PCH(methyl)CH(methyl)P(phenyl)$_2$, prepared in Catalyst Preparation Example 1, and 3 mmol of MMAO-12, manufactured by Akzo-Nobel Corp., at a reaction temperature of 45° C. and an ethylene pressure of 30 bar for reaction times of 30 minutes (Example 9), 1 hour (Example 10), 2 hours (Example 11) and 4 hours (Example 12). Otherwise, the reaction process and product treatment processes were conducted as in Example 1.

Figure 2:
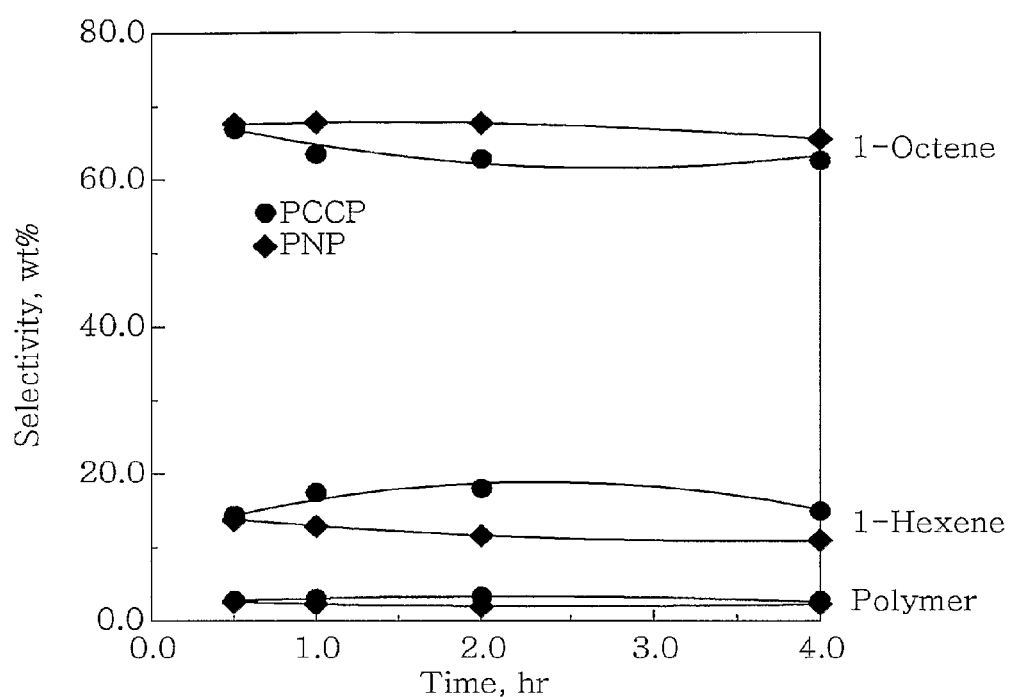
FIG. 2 is a graph showing the change in selectivity in the ethylene tetramerization reaction using a catalyst system according to the present invention.

The results of tetramerization of ethylene in Examples 9 to 12 are given in Table 2, and the changes in reaction activity and selectivity depending on reaction time are shown in FIGS. 1 and 2.

Comparative Examples 14 to 17

Changes in reaction activity and selectivity depending on reaction time in the tetramerization of ethylene using Cr(III)(acetylacetonate)$_3$, (phenyl)$_2$PN(isopropyl)P(phenyl)$_2$ and MMAO-12

The tetramerization of ethylene was conducted as in Examples 9 to 12, except that 2.1 mg (0.005 mmol) of (phenyl)$_2$PN(isopropyl)P(phenyl)$_2$ of Comparative Catalyst Preparation Example 1 was used instead of (phenyl)$_2$PCH(methyl)CH(methyl)P(phenyl)$_2$.

The results of tetramerization of ethylene in Comparative Examples 14 to 17 are given in Table 2, and the changes in reaction activity and selectivity depending on reaction time are shown in FIGS. 1 and 2.

TABLE 2

Results of tetramerization of ethylene depending on reaction time

|  | Reaction time (hr) | Product (g) | 1-C6 (%) | 1-C8 (%) | Polymer (%) |
|---|---|---|---|---|---|
| Exp. 9 | 0.5 | 36.0 | 14.5 | 68.6 | 2.3 |
| Exp. 10 | 1 | 50.7 | 17.7 | 65.0 | 2.5 |
| Exp. 11 | 2 | 81.3 | 18.5 | 64.3 | 3.0 |
| Exp. 12 | 4 | 138.4 | 15.5 | 64.5 | 2.8 |
| Co. Exp 14 | 0.5 | 40.8 | 13.8 | 69.4 | 2.0 |
| Co. Exp 15 | 1 | 51.3 | 13.2 | 69.5 | 1.5 |
| Co. Exp 16 | 2 | 64.0 | 12.1 | 69.4 | 2.0 |
| Co. Exp 17 | 4 | 69.3 | 11.1 | 67.5 | 2.5 |

Examples 9 to 12 and Comparative Examples 14 to 17 were conducted to compare the 1-octene production yields of the P—C—C—P backbone structure ligand of the present invention with those of the conventional hetero atom structure PNP ligand depending on reaction times.

FIG. 1 shows the change of catalytic activity in the tetramerization of ethylene depending on reaction time. As shown in FIG. 1, it can be seen that when the catalyst system comprising the P—C—C—P backbone structure ligand according to the present invention is used, the yield of 1-octene is constantly increased with the passage of time, but when the conventional catalyst system comprising the PNP ligand is used, the yield of 1-octene is first increased, but then decreases as the reaction progresses. That is, it can be seen that the catalyst system comprising the P—C—C—P backbone structure ligand according to the present invention can maintain stable catalytic activity better than the conventional catalyst system comprising the PNP ligand.

FIG. 2 is a graph showing the selectivity in the tetramerization of ethylene depending on reaction time. As shown in FIG. 1, it can be seen that both the catalyst system comprising the P—C—C—P backbone structure ligand according to the present invention and the conventional catalyst system comprising the PNP ligand exhibit a high 1-octene selectivity of 60% or more.

Accordingly, in the tetramerization of ethylene, it can be seen that the catalyst system comprising the P—C—C—P backbone structure ligand according to the present invention has the same catalytic activity and selectivity as the conventional catalyst system, and that it can stably maintain catalytic activity better than the conventional catalyst system.

The invention claimed is:

1. A method of preparing 1-octene by tetramizing ethylene using the following catalyst system consisting essentially of:
   chromium or chromium compound,
   an alkylaluminoxane cocatalyst, and
   a P—C—C—P backbone structure ligand represented by Formula 1 below:

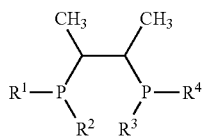

[Formula 1]

wherein R1, R2, R3 and R4 are each independently a hydrocarbyl group, a substituted hydrocarbyl group, a heterohydrocarbyl group and a substituted heterohydrocarbyl group, and each of the R1, R2, R3 and R4 has no substituent on atoms adjacent to the atoms bonded with P atoms.

2. The method of preparing 1-octene by tetramizing ethylene of claim 1, wherein the method is operated at a temperature of −20-250° C.

3. The method of preparing 1-octene by tetramizing ethylene of claim 1, wherein the method is operated at a temperature of 15-130° C.

4. The method of preparing 1-octene by tetramizing ethylene of claim 1, wherein the method is operated at a temperature of 30-70° C.

5. The method of preparing 1-octene by tetramizing ethylene of claim 1, wherein the method is operated at a pressure of atmospheric pressure-500 bar.

6. The method of preparing 1-octene by tetramizing ethylene of claim 1, wherein the method is operated at a pressure of 10-70 bar.

7. The method of preparing 1-octene by tetramizing ethylene of claim 1, wherein the method is operated at a pressure of 30-50 bar.

8. The method of preparing 1-octene by tetramizing ethylene of claim 1, wherein the method is operated using inactive solvent selected from saturated aliphatic hydrocarbons, unsaturated aliphatic hydrocarbons, aromatic hydrocarbons, halogenated hydrocarbons, or a combination thereof.

9. The method of preparing 1-octene by tetramizing ethylene of claim 8, wherein the inactive solvent selected from benzene, toluene, xylene, cumene, heptanes, cyclohexane, methylcyclohexane, methylcyclopentane, n-hexane, 1-hexene or a combination thereof.

10. The method of preparing 1-octene by tetramizing ethylene of claim 1, wherein the aluminum of alkylaluminoxane : chromium or chromium compound is 1:1-10,000:1.

11. The method of preparing 1-octene by tetramizing ethylene of claim 1, wherein the aluminum among alkylaluminoxane : chromium or chromium compound is 1:1-1,000:1.

* * * * *